United States Patent [19]

Quinn

[11] Patent Number: 5,451,216
[45] Date of Patent: Sep. 19, 1995

[54] NON-OCCLUDING CATHETER BOLUS

[75] Inventor: David G. Quinn, Grayslake, Ill.

[73] Assignee: Radius International Limited Partnership, Grayslake, Ill.

[21] Appl. No.: 217,446

[22] Filed: Mar. 24, 1994

Related U.S. Application Data

[63] Continuation-in-part of Ser. No. 77,019, Jun. 15, 1993.

[51] Int. Cl.$^6$ .............................................. A61M 25/00
[52] U.S. Cl. ................................... 604/270; 604/280; 604/283
[58] Field of Search ..................... 604/270, 280–281, 604/264, 275, 268, 266; 433/91, 96

[56] References Cited

U.S. PATENT DOCUMENTS 4,594,074  6/1986  Andersen et al. .

*Primary Examiner*—C. Fred Rosenbaum
*Assistant Examiner*—Perry E. Van Over
*Attorney, Agent, or Firm*—Willian Brinks Hofer Gilson & Lione

[57] ABSTRACT

An improved catheter for delivering fluid to a body cavity or aspirating the cavity. The catheter includes a cylindrical tube having a proximal end for joining the tube to a source of fluid or suction and a distal end connected to a bolus. The bolus includes a tubular shaped body formed of semi-rigid plastic. The body includes a tube connector section at one end, a tip section at the other end and a passage section between the connector section and the tip section. The passage section also contains a radial passage portion adjacent the tip section that forms a port through the side of the body. The port extends around more than 180 degrees of the circumference of the body. A bolus body segment forms a portion of the passage section opposite the port and connects the tip section with the tube connector section. The body segment includes side walls having a height which is less than 50 percent of the outside radius of the body. The body segment includes an arcuate base in the radially extending passage portion below the port. The body segment also includes a structural component protruding radially outwardly therefrom that is effective to prevent the body segment from bending and restricting the port.

4 Claims, 4 Drawing Sheets

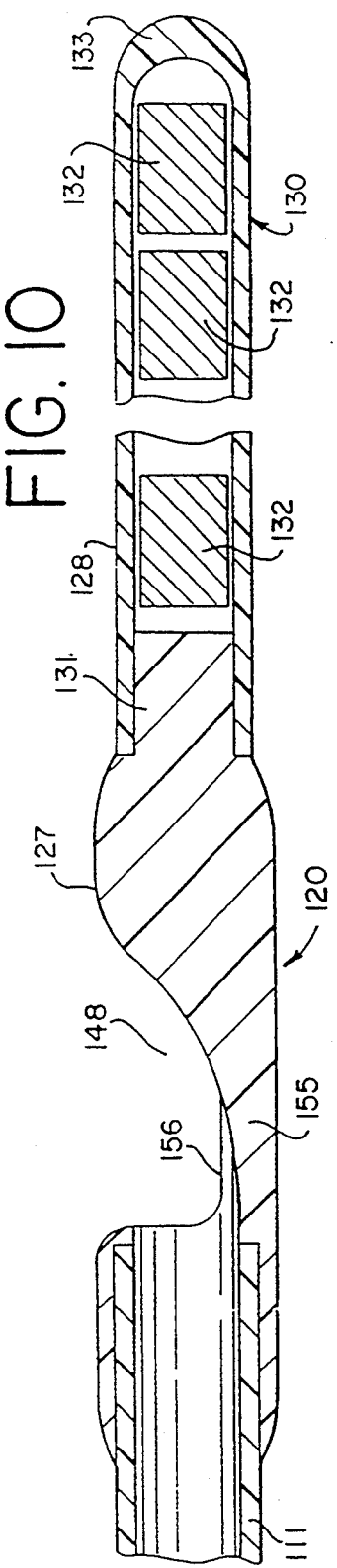
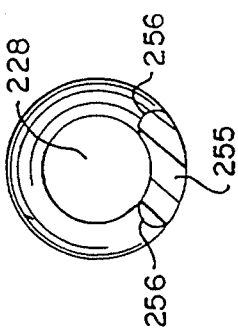
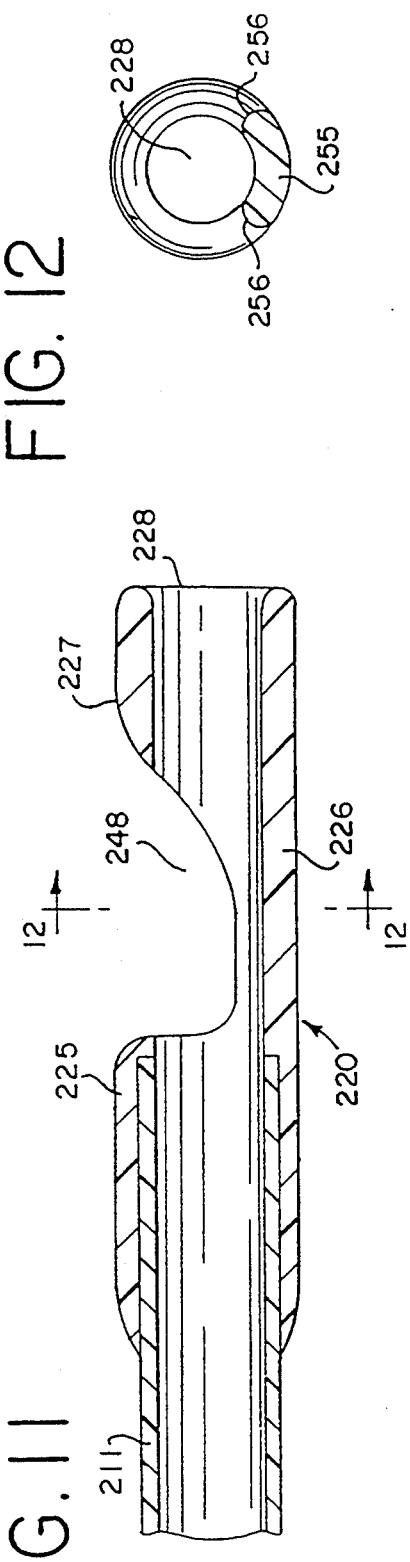
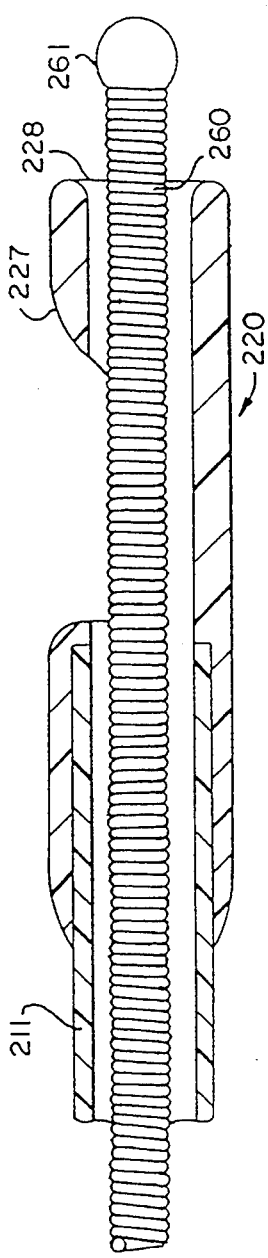

NON-OCCLUDING CATHETER BOLUS

RELATED APPLICATIONS

This application is a continuation-in-part of copending U.S. patent application Ser. No. 08/077,019, filed on Jun. 15, 1993 in the names of David G. Quinn, Charles M. Crabtree and David S. MacLean. The disclosure of Ser. No. 08/077,019 is hereby incorporated by reference.

FIELD OF THE INVENTION

This invention relates generally to catheters for use in administering fluids to body cavities, irrigating the cavities and aspirating them. It relates particularly to catheter tubes and, more specifically, to the distal ends thereof which contain the opening(s) for fluid egress or ingress.

BACKGROUND OF THE INVENTION

Catheters are commonly used for enteral feeding, urinary bladder drainage and irrigation, suctioning of blood and mucous, as well as for other purposes in the medical treatment of humans. Exemplary catheters are illustrated and described in U.S. Pat. Nos. 4,594,074, 4,410,320, 4,390,017, 4,388,076, and 4,220,542. Each of these catheters employs a tube with a distal end opening, either axially through the tube end or through its side.

In the type of catheter illustrated in U.S. Pat. No. 4,594,074, the distal end of the catheter tube is provided with a tip or bolus, as it is called, in which a side opening is formed. The bolus has a generally cylindrical passage in it with an internal diameter corresponding to the internal diameter of the tube on which it is mounted. The bolus opening or port is formed through its side wall and the side wall, on each side of the opening, is generally vertical, i.e., those side wall portions bracketing the opening extend parallel to each other. This configuration produces a bolus in which the side wall, at the opening, encloses at least 180° of the inside circumference of the passage in the bolus. In addition to having a bolus opening or port of the aforedescribed nature and configuration, the floor of the passage below the port curves upwardly on an arc of substantial radius. The result attributed to this bolus design is a fluid flow characteristic which substantially approximates the fluid flow characteristics of an open-ended tube, yet does not become occluded with mucous or feeding material.

The tube and bolus designs illustrated and described in the aforementioned patents, including U.S. Pat. No. 4,594,074, all have at least one drawback, however. When used in an aspiration mode in the stomach or bladder, for example, the bolus opening or port may become clogged, either by mucosa in the stomach or the wall of the bladder. This is true notwithstanding the fact that the very purpose of the bolus design in the '074 patent, for example, is to avoid such malfunctions, because the port can be bridged too easily transversely of the bolus by the occluding surface.

SUMMARY OF THE INVENTION

A primary object of the present invention is to provide an improved bolus for a catheter tube.

Another object is to provide an improved side-opening bolus for a catheter tube.

Still another object is to provide a side-opening catheter bolus which essentially defies occlusion during all modes of operation including, particularly, the aspiration mode.

A further object is to provide a side-opening catheter bolus which is simpler in construction, more compact, and less expensive than catheter tube boluses presently in use.

The foregoing and other objects are realized in accord with the present invention by providing a catheter and bolus for delivering or suctioning fluids to the body cavity of a patient. The catheter includes a tube with a proximal end for joining it to a source of fluid or suction and a distal end connected to a bolus. The bolus has a tubular shaped body with a tube connector section at one end, a nose section at the other end and a passage section between the connector and nose sections. The bolus body has an irregularly shaped lower surface. In one aspect of the present invention the irregularly shaped surface forms an arch.

BRIEF DESCRIPTION OF THE DRAWINGS

The invention, including its construction and method of operation, is illustrated more or less diagrammatically in the drawings, in which:

FIG. 10 is an enlarged side view, partially in section, of the bolus end of a catheter showing a modification of the first form of bolus embodying features of the present invention;

FIG. 11 is an illustration of a catheter including a bolus embodying features of a second form of the invention;

FIG. 12 is a sectional view taken along line 12—12 of FIG. 11;

FIG. 13 is a view similar to FIG. 11 showing a guide wire in place in the bolus;

DESCRIPTION OF THE PREFERRED EMBODIMENTS

The preferred embodiments are described here in the context of catheters, generally. The principles of the invention apply equally well to all types of catheters, including Foley catheters, urethral catheters and catheters for use in such diverse applications as intravenous, pharyngeal, esophageal, rectacolonic, choledochal, gastric, nasal and endobronchial procedures, as well as others.

Figure 1:
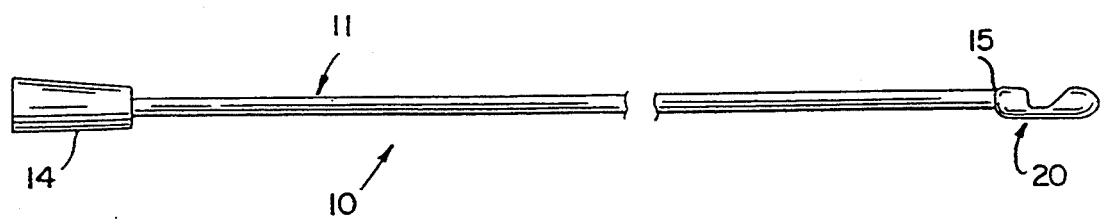
FIG. 1 is an illustration of a catheter which might be used for enteral feeding or aspiration, including the catheter tube and a bolus embodying features of a first form of the present invention.
Figure 2:
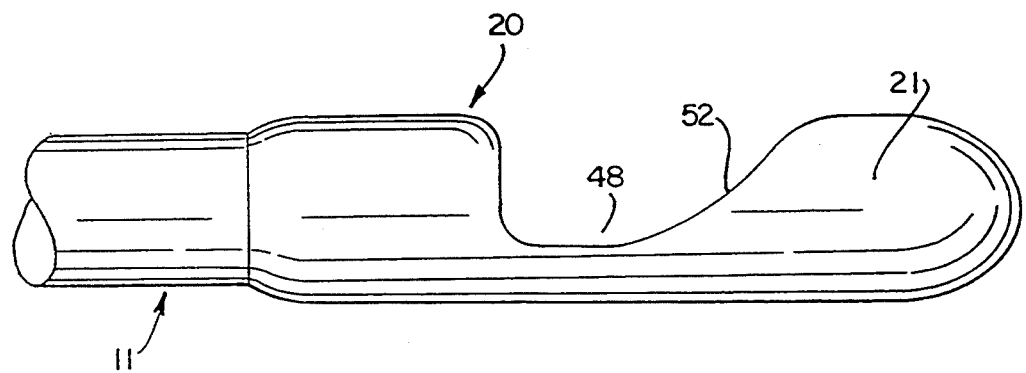
FIG. 2 is an enlarged side view of the bolus end of the catheter seen in FIG. 1, showing the bolus connected to the catheter tube.
Figure 3:
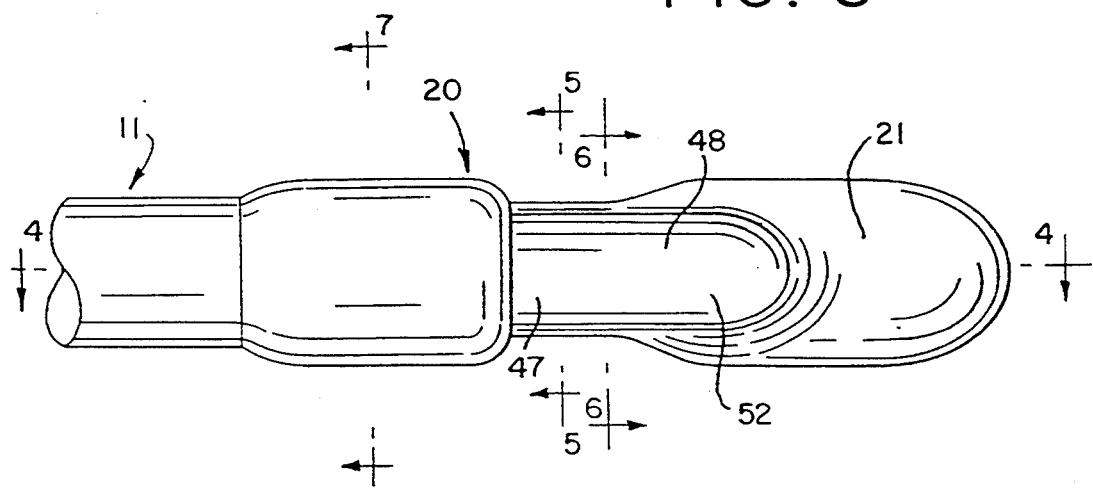
FIG. 3 is a top plan view of the bolus end of the catheter seen in FIG. 2.

Referring now to the drawings, and particularly to FIG. 1, a catheter is seen generally at 10. The catheter 10 includes a cylindrical tube 11 which is preferably fabricated from a resilient, biocompatible plastic such as polyurethane. Although other plastics, including polyvinyl chloride, may be used, the properties of polyurethane are such that it can be fabricated with maximum inside tube diameter and minimum tube wall thickness. It also has a high resistance to highly acidic fluids frequently encountered in clinical applications. Thermoset materials such as silicone may also be used.

The tube 11 extends between a proximal end 14, which may be connected to a syringe for use in aspiration applications or for administrations of fluid, and a terminal end 15. A bolus 20 embodying features of a first form of the present invention is seated in the terminal end 15 of the tube 11.

Referring now to FIGS. 2–7, the bolus 20 and its connection to the terminal end 15 of the catheter tube 11 are shown in greater detail. The bolus has a generally tubular-shaped body 21 fabricated of semi-rigid polyurethane. The polyurethane used for the bolus body 21 has a durometer reading which is preferably in the range of 42 D (or 90 A) to 70 D.

The dimensions of the body 21 vary with the size of the catheter tube in use. Catheter tubes are specified within a standard series of sizes known as "French" sizes. French (FR) sizes designate tubes by their outside diameter. The smallest designation is 3 FR, which has an outside diameter of 1 mm or 0.039". The catheter tube 11 which is utilized in describing the first form of the present invention is an 8 FR tube. This tube in polyurethane has an outside diameter of 0.108". The tube has an inside passage diameter of 0.078".

In this embodiment of the invention, the tubular shaped body 21 of the bolus 20 for an 8 FR size tube 11 has an overall length of 0.580 inches and an outside diameter of 0.138 inches. The outside diameter of the body 21 is, thus, slightly larger than that of the tube 11 to which is it connected.

The body 21 of the bolus 20 is formed unitarily, by injection molding, but comprises three distinct body sections. These are the tube glue-area section 25, the flow passage section 26 and the bullet tip section 27.

Figure 4:
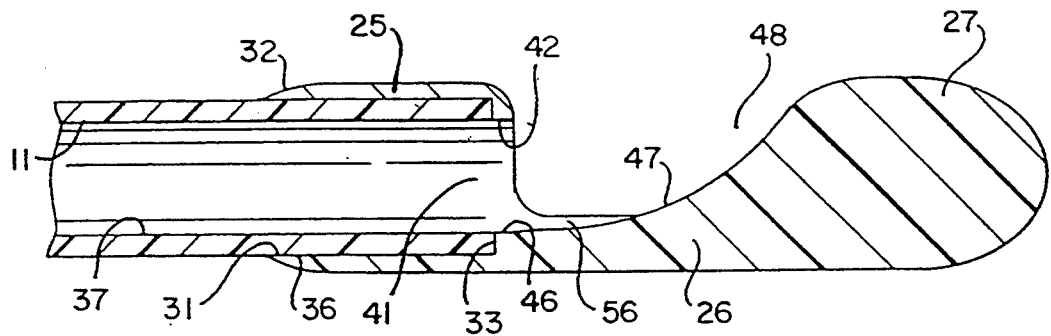
FIG. 4 is a longitudinal sectional view taken along line 4—4 of FIG. 3.

As best seen in FIG. 4, the terminal end 15 of the tube 11 connects to the bolus 20 by seating in a cylindrical bore 31 formed axially into the proximal end 32 of the bolus. The cylindrical bore 31 extends 0.185 inches axially into the bolus 21, where it terminates in a shoulder 33. The axial length of the bore 31 forms the tube glue area section 25 of the bolus.

The cylindrical bore 31 has an inside diameter equal to the diameter of the outside surface 36 of the tube 11. The terminal end of the tube 11 is press fit into the bore 31 until it abuts the shoulder 33 and is glued in this position. In this relationship of the tube 11 to the bolus 20, the inner surface 37 of the tube passage is flush with a correspondingly shaped passage 41 in the flow-passage section 26 of the bolus body 21 or, more precisely, with the inner surface 42 of that passage 41, so that fluid flow between the tube and the bolus 20 is turbulence free.

The passage 41 comprises two passage portions, a short cylindrical portion 46 extending axially of the bolus body 21 and a longer portion 47 which curves radially away from the axis of the body 21 and, through a side opening 48 in the body, forms the fluid ingress and egress port for the bolus 20 and the tube 11.

Figure 5:
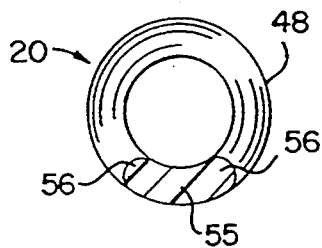
FIG. 5 is a transverse sectional view taken along line 5—5 of FIG. 3.
Figure 6:
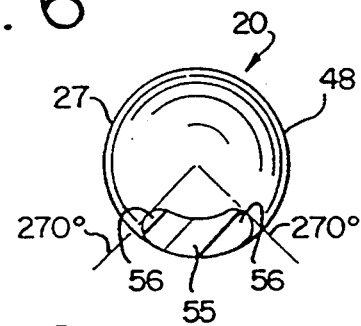
FIG. 6 is a transverse sectional view taken along line 6—6 of FIG. 3.
Figure 7:
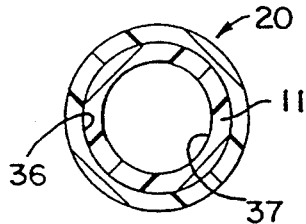
FIG. 7 is a transverse sectional view taken along line 7—7 of FIG. 3.

As best seen in FIGS. 4–6, the shape of the passage portion 47 determines the shape of the side opening or port 48. The port 48 is formed by removal of a piece of the bolus body 21 around 270° of the circumference of the body to create the port 48. At the same time, directly opposite the center of the port 48, the floor 52 of the passage segment 47 is built up progressively in the direction of the bullet tip section 27 of the bolus body 21, so as to define a uniform arc terminating at the outer surface of the bolus body.

The radius of the arc of the floor 52 is relatively short. It must be at least as large as the inside diameter of the bolus passage segment 46. However, it should be less than 5 times that diameter and is preferably between 2.5 and 3.75 times that diameter. In the 8 FR tube version shown in FIGS. 2–9, with an inside diameter of 0.078 inches, the radius of the floor 52 shown is 3.25 times 0.078 inches, or 0.254 inches, for example. The length of the port 48 is then 0.180 inches in this example.

As seen in FIGS. 5 and 6, the aforedescribed formation of the port 48 by removal of a piece of the bolus body around 270° of the circumference of the body leaves a bolus body segment 55 opposite the port, effectively connecting the bullet-tip section 27 of the bolus with the tube glue-area section 25. This body segment 55 forms a bottom wall 57 directly opposite the port 48 and a short side wall 56 on each side of the bottom wall and of the flow passage portion 47 in the flow passage section 26. According to the invention, the overall height of these side walls 56 is 29 percent of the radius (outside) of the tube 11 being used, regardless of what the French size of the tube is.

Figure 9:
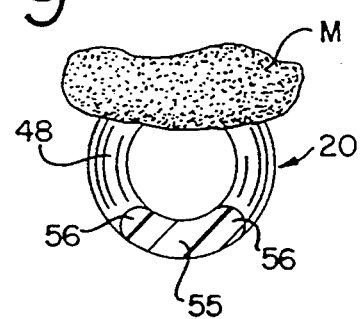
FIG. 9 is a sectional view taken along line 9—9 of FIG. 8.
Figure 8:
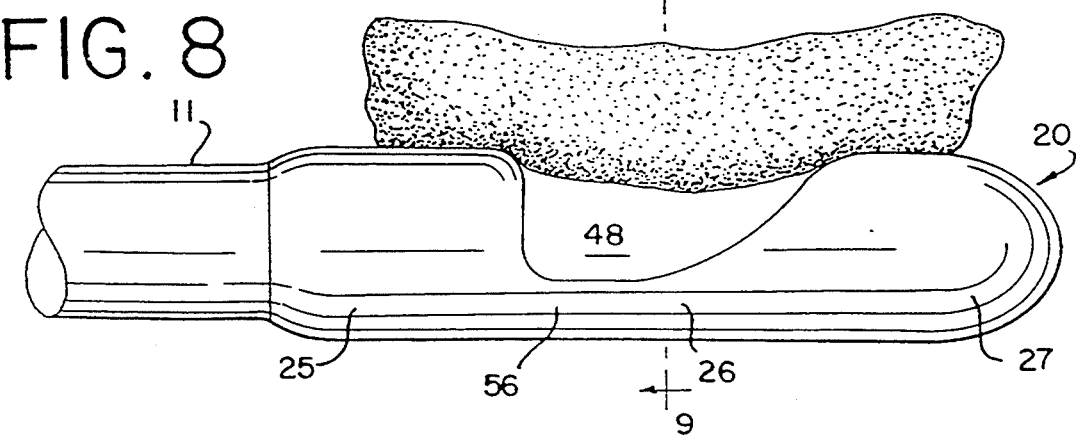
FIG. 8 is a view similar to FIG. 2 showing mucosa pressed against the bolus side port and yet not obstructing the port to a measurable extent.

Referring now to FIGS. 8 and 9, the catheter 10 including a bolus 20 embodying features of a first form of the present invention is illustrated in use. Catheter 10 insertion has positioned the bolus 20 with its port 48 against the mucosa M in a patient's stomach, for example. Notwithstanding this positioning, the port 48 is unblocked, as influx arrows in FIG. 9 illustrate. The combination of a port 48 with maximum circumferential width (270°) and stiff, short body segment 55 forming the sidewalls 56 produces a virtually non-occludable bolus 20.

Turning to FIG. 10, a modification of the bolus 20 embodying a first form of the invention is seen generally at 120. Corresponding reference numerals plus 100 digits are used to identify corresponding components. The bolus 120 is identical to the bolus 20 hereinbefore dismissed except for the fact that its bullet-tip section 127 has an extended nose 128, and that nose is weighted.

A catheter with a weighted nose is sometimes used to assist in proper positioning of the bolus in a patient's stomach, for example. In the bolus 120 that is accomplished by using the extended nose 128 comprising a polyurethane sleeve 130 glued to a mounting extension 131 on the bolus. The sleeve 130 is then filled with tungsten cylinders 132 which are held in place by the segmentally spherical cap 133 which is formed by heat on the end of the sleeve.

A bolus embodying a second form of the present invention is illustrated generally at 220 in FIGS. 11–13. Where components correspond to those of the bolus 20, they are identified by corresponding reference numerals plus 200 digits. Here the bolus 220 is illustrated in association with a 6 FR tube, i.e., one smaller in diameter than the 8 FR tube discussed in relation to the first embodiment. As such, the bolus 220 is proportionally smaller than those (20 and 120) of the first embodiment.

The bolus 220 differs from the bolus 20 only in that its tip section 227 is not bullet shaped but is, in itself, an open-ended tubular section. Its free end 228 is open through to the side-opening port 248, as illustrated.

The purpose of this construction, as seen in FIG. 13, is to permit the use of a guide wire 260 extending through the catheter tube 211 and out the open end 228 of the tip section 227. The guide wire 260 has a ball-shaped free end 261.

The guide wire 260 is used to guide the catheter 210 with the bolus 220 out of the stomach and into the jejunum or duodenum. The wire 260, which is relatively stiff compared to the catheter tube 211, is inserted ahead of the bolus 220 and then the catheter 210 is slipped downwardly over it to properly position the bolus before the wire is removed.

In addition to facilitating insertion of a bolus embodying features of the invention over a guide wire, the bolus 220 configuration also provides marked advantages in application on a suction catheter. Suction effective through the open free end 228 and the side-opening port 248 is not easily blocked. The open free end 228 and the port 248 effectively provide blockage relief for each other.

Figure 14:
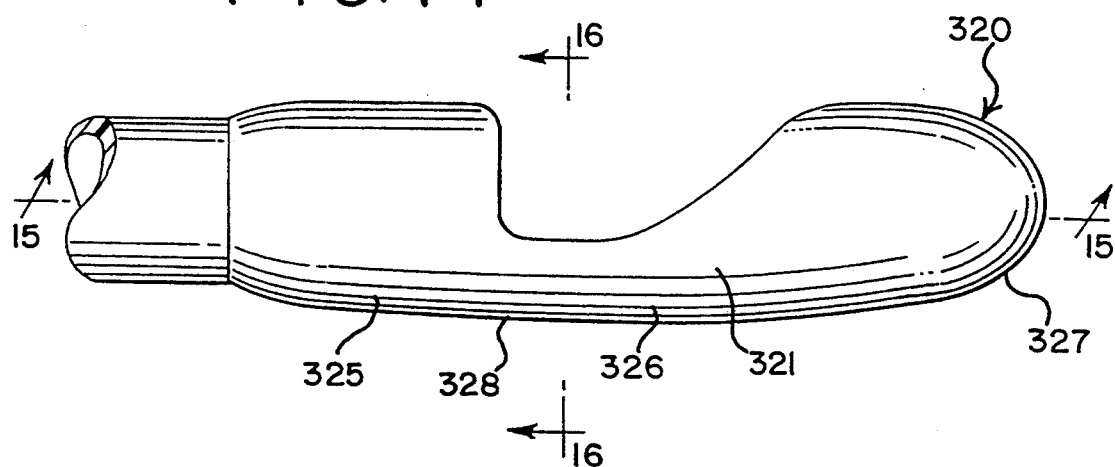
FIG. 14 is an illustration of a catheter including a bolus embodying features of a third form of the invention.
Figure 15:
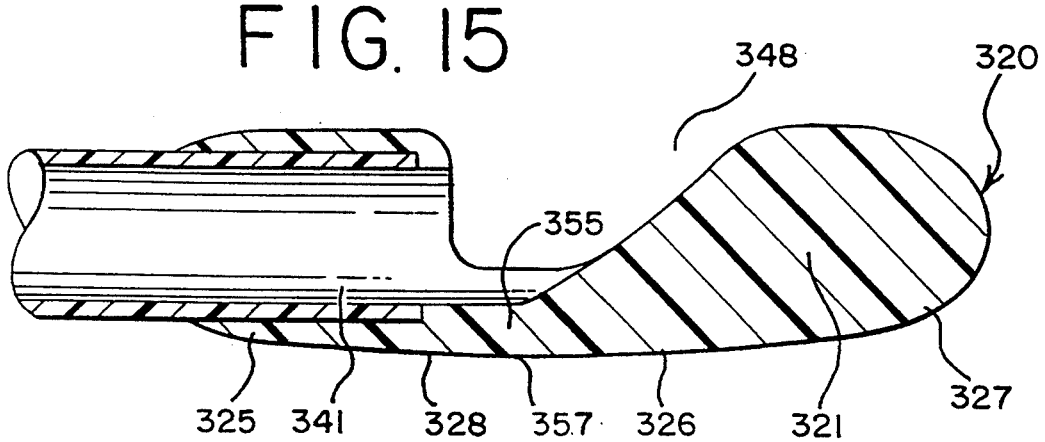
FIG. 15 is a sectional view taken along line 15—15 of FIG. 14.
Figure 16:
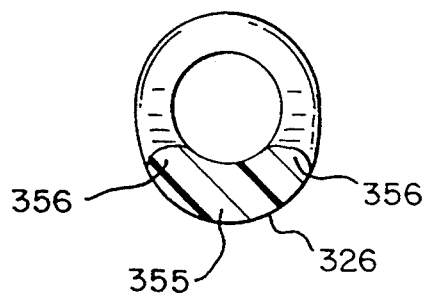
FIG. 16 is a sectional view taken along line 16—16 of FIG. 14.

A bolus embodying a third form of the present invention is illustrated generally at 320 in FIGS. 14–16. Where components correspond to those of the bolus 20, they are identified by corresponding reference numerals plus 300 digits. Here, the bolus 320 is illustrated in association with an 8 FR tube, i.e. the same diameter as the tube shown in the first embodiment (20 and 120) and having a larger diameter than the 6 FR tube shown in the second embodiment.

The bolus 320 differs from the bolus 20 in that its body 321 includes an arch 328 which distends the lower surface of the body downwardly and extends longitudinally of the bolus under the flow passage section 326. The arch 328 which thus forms a somewhat bulbous or irregularly shaped surface on the body 321 opposite the port 348, increases the stiffness or rigidity of the body segment 355 including its bottom wall 357 and the side walls 356. The arch 328 is important because it prevents the body segment 355 from bending and possibly blocking the passage 341.

As shown in FIGS. 14 and 15 longitudinally of the body 321 the arch 328 begins in the glue area section 325 and increases in thickness until a maximum thickness or peak is achieved in the flow passage section 326. After reaching a maximum thickness or peak at the center, the arch decreases in thickness and preferably terminates just prior to the bullet tip in the section 327. While the exact postioning of the peak may be varied, the peak should be in the region of the body segment 355 so as to support that portion of the bolus 320.

As shown in FIG. 16, the thickest point of the arch 328 is also in the bottom wall 357 of the transverse center of the arch 328. In other words, the arch 328 decreases in thickness as it extends laterally around the bottom wall 357 of the body segment 355 and up its side walls 356.

The thickness and the length of the arch 328 may be varied depending upon the size of the bolus used. In the 8 FR tube, for example, the middle of the arch preferably has a thickness of 0.015 inches. Furthermore, the arch 328 preferably has a length of 0.468 inches.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

I claim:

1. In a catheter for delivering fluid to a body cavity or aspirating said cavity wherein said catheter includes a cylindrical tube having a proximal end for joining said tube to a source of fluid or suction and a distal end connected to a bolus, an improved bolus comprising:
   a) a tubular shaped body formed of semi-rigid plastic;
   b) said body including a tube connector section at one end, a tip section at the other end and a passage section between said connector section and said tip section, said passage section containing a radial passage portion adjacent said tip section, said radial passage portion forming a port through said side of said body;
   c) a bolus body segment in the passage section opposite said port, said body segment connecting said tip section with said tube connector section;
   d) said body segment forming a side wall in each side of said passage section, each side wall having a height which is less than 50 percent of the outside radius of said body, whereby said port extends around more than 180 degrees of the circumference of said body;
   e) said body segment forming an arcuate base in said radially extending passage portion below said port;
   f) said body segment aim including a structural component protruding radially outwardly therefrom, and effective to prevent said body segment from bending and restricting said port.

2. The improved bolus of claim 1 further characterized in that:
   a) said structural component forms an arch which underlies said passage section and portions of said tube connector section and said tip section.

3. The improved bolus of claim 2 further characterized in that:
   a) said arch is orientated longitudinally of said body.

4. The improved bolus of claim 3 further characterized in that:
   a) said arch has a maximum thickness beneath said bottom wall of said body segment and decreases in thickness around said side walls towards said port.

* * * * *

UNITED STATES PATENT AND TRADEMARK OFFICE
CERTIFICATE OF CORRECTION

PATENT NO. : 5,451,216
DATED : September 19, 1995
INVENTOR(S) : David G. Quinn

It is certified that error appears in the above-indentified patent and that said Letters Patent is hereby corrected as shown below:

In claim 1, line 25, delete "aim" and substitute --also--.

In claim 3, line 3, delete "orientated" and substitute --oriented--.

In claim 4, line 3, delete the second occurrence of "said" and substitute --a--.

Signed and Sealed this

Sixth Day of May, 1997

*Attest:*

BRUCE LEHMAN

*Attesting Officer*     *Commissioner of Patents and Trademarks*